United States Patent
Rosa-Bray et al.

(10) Patent No.: US 10,391,223 B2
(45) Date of Patent: Aug. 27, 2019

(54) USE OF PLASMAPHERESIS TO TREAT BLOOD PRESSURE DISORDERS

(71) Applicant: GRIFOLS WORLDWIDE OPERATIONS LIMITED, Dublin (IE)

(72) Inventors: Marilyn Rosa-Bray, Bellevue, WA (US); Shinji Wada, Arcadia, CA (US)

(73) Assignee: Grifols Worldwide Operations Limited, Dublin (IE)

( * ) Notice: Subject to any disclaimer, the term of this patent is extended or adjusted under 35 U.S.C. 154(b) by 158 days.

(21) Appl. No.: 14/727,403

(22) Filed: Jun. 1, 2015

(65) Prior Publication Data
US 2015/0343130 A1 Dec. 3, 2015

Related U.S. Application Data (60) Provisional application No. 62/006,999, filed on Jun. 3, 2014.

(51) Int. Cl.
*A61M 1/34* (2006.01)
*A61M 1/36* (2006.01)

(52) U.S. Cl.
CPC .......... *A61M 1/3496* (2013.01); *A61M 1/3693* (2013.01); *A61M 2230/30* (2013.01)

(58) Field of Classification Search
CPC .................. A61M 1/3496; A61M 2230/30
See application file for complete search history.

(56) References Cited

U.S. PATENT DOCUMENTS

| | | | |
|---|---|---|---|
| 4,350,156 | A | 9/1982 | Malchesky |
| 4,374,731 | A | 2/1983 | Brown |
| 4,540,401 | A | 9/1985 | Marten |
| 4,657,529 | A | 4/1987 | Prince |
| 5,919,902 | A | 7/1999 | Becker |
| 6,248,238 | B1 | 6/2001 | Burtin |
| 6,423,022 | B1 | 7/2002 | Roeher |
| 6,551,266 | B1 | 4/2003 | Davis |
| 6,627,151 | B1 | 9/2003 | Borberg |
| 7,402,246 | B2 | 7/2008 | Bomberger |
| 8,048,015 | B2 | 11/2011 | Bellotti |
| 8,480,607 | B2 | 7/2013 | Davies |
| 2005/0051497 | A1 | 3/2005 | Latino |
| 2007/0181499 | A1 | 8/2007 | Roberts |
| 2010/0038317 | A1 | 2/2010 | Bissler |

(Continued)

FOREIGN PATENT DOCUMENTS

| | | |
|---|---|---|
| WO | 86000231 | 1/1986 |
| WO | 2011015380 | 2/2011 |

(Continued)

OTHER PUBLICATIONS

Glasson ("Treatment of arterial hypertension by plasmapheresis" Scweiz Med Wochenschr, Feb. 5, 1983; 113(5):abstract).*

(Continued)

*Primary Examiner* — Ryan B Huang
(74) *Attorney, Agent, or Firm* — Dinsmore & Shohl LLP (57) ABSTRACT

A method of treating a blood pressure disorder comprises identifying a patient having a blood pressure disorder, and administering a treatment regime comprising two or more rounds of plasmapheresis to the patient, wherein the treatment regime lowers blood pressure in the patient.

20 Claims, 4 Drawing Sheets

(56) References Cited

U.S. PATENT DOCUMENTS

| | | |
|---|---|---|
| 2010/0105990 A1 | 4/2010 | Bene |
| 2010/0192686 A1 | 8/2010 | Kamen |
| 2010/0316730 A1 | 12/2010 | Latino |
| 2011/0142700 A1 | 6/2011 | Gura |
| 2012/0165685 A1* | 6/2012 | Weasler ............. A61B 5/02042 600/485 |
| 2013/0046225 A1 | 2/2013 | Nose |
| 2013/0202601 A1 | 8/2013 | Fornoni |
| 2013/0236559 A1* | 9/2013 | Grifols Lucas ..... A61M 1/3496 424/529 |

FOREIGN PATENT DOCUMENTS

| | | |
|---|---|---|
| WO | 2011080191 | 7/2011 |
| WO | 2012109282 | 8/2012 |

OTHER PUBLICATIONS

Halperin et al. ("Dyslipidemia and the risk of incident hypertension in men" Hypertension, Jan. 2006, 47:45-50).*

Carretero et al. ("Clinical cardiology: new frontiers" Circulation 2000; 101:329-335).*

Ananchenko et al. ("Plasmapheresis in the treatment of patients with hypertension" Soy Med; 1991; 10:abstract).*

Heidland and Schaefer ("Pathophysiology and treatment of hypertension in dialysis patients" New Perspectives in Hemodialysis, Peritoneal Dialysis, Arteriovenous Hemofiltration, and Plasmapheresis; Horl et al. (eds.); 1989:79-91).*

Glasson "Treatment of arterial hypertension with plasmapheresis" Scweiz Med Wochenschr, Feb. 5, 1983; 113(5) (Year: 1983).*

Title 21-Food and Drugs "Part 640—Additional Standards for Human Blood and Blood Products; Subpart G-Source Plasma, §640.65-Plasmapheresis(b)(4)-(8)"; (https://www.accessdata.fda.gov/scripts/cdrh/cfdocs/cfcfr/CFRSearch.cfm?fr=640.65; accessed Jan. 10, 2017). (Year: 2017).*

U.S. Final Office Action for U.S. Appl. No. 13/418,123, dated Oct. 20, 2016, 15 pages.

ATP III Final Report: Appendix III-A Distributions of Total Cholesterol, LDL Cholesterol, HDL Cholesterol, and Triglycerides in the U.S. Adult Population, NHANES III Data (1988-1994) (Serum), (http://circ.ahajournals.org/content/106/25/3237/5tab-figures-data, accessed Oct. 5, 2016, published Dec. 17, 2002, 14 pages.

Atsma et al., Cardiovascular and demographic characteristics in whole blood and plasma donors; results from the donor InSight study; Transfusion, vol. 51, Issue 2, pp. 412-420, Feb. 2011, 16 pages.

B. Braun website, http://ww.bbraun.com/cps/rde/xchg/bbraun-com/hs.xsl/apheresis-01.html, Wayback version 2009.

Bechtloff, S. et al., "A prospective trial on the safety of long-term intensive plasmapheresis in donors," 2005, pp. 189-195, vol. 88, Vox Sanguinis.

Beigel, R. et al., Homozygous familial hypercholesterolemia: Long term clinical course and plasma exchange therapy for two individual patients and review of the literature, 2009, pp. 219-224, vol. 24, Journal of Clinical Apheresis.

Bell, K. et al., "Monitoring adherence to drug treatment by using change in cholesterol concentration: secondary analysis of trial data," 2011, pp. 1-7, vol. 342, British Medical Journal.

Bookstein, L. et al., "Day-to-day variability of serum cholesterol, triglyceride, and high-density lipoprotein cholesterol levels," 1990, pp. 1653-1657, vol. 150, Archives of Internal Medicine.

Burnouf, T., et al., "Protein composition and activation markers in plasma collected by three apheresis procedures," 2003, pp. 1223-1229, vol. 43, Transfusion.

Cohen, M, et al., "Safety and long-term effects of plasmapheresis," 1970, pp. 58-66, vol. 10, No. 2, Transfusion.

Dechmann-Sultemeyer, T. et al., "Tandem plasmapheresis and haemodialysis as a safe procedure in 82 patients with immune-mediated disease," 2009, pp. 252-257, vol. 24, Nephrology Dialysis Transplantation.

Eason, S. et al., " Experience with routine total nonfasting blood cholesterol screening of volunteer blood and component donors," 2011, pp. 731-736, vol. 51, Transfusion.

Edgren, G. et al., "Donation frequency, iron loss, and risk of cancer among blood donors," Apr. 16, 2008, pp. 572-579, vol. 100, No. 8, Journal National Cancer Institute.

Evans, K., "Low-density lipoprotein apheresis in patients with severe familial hypercholesterolemia refractory to, or intolerant of, lipid-lowering drug therapy: preventing the onset or progression of cardiovascular disease," Capstone project and theses dissertation, School of Physician Assistants, Pacific University, 2011.

Glaszlou, P, et al., "Monitoring cholesterol levels: measurement error or true change?" May 6, 2008, pp. 656-661, vol. 148, No. 9, Annals of Internal Medicine.

Irwig, L. et al., "Estimating an individual's true cholesterol level and response to intervention," Sep. 25, 1991, pp. 1678-1685, vol. 266, No. 12, JAMA.

Ito, M. et al., "Management of familial hypercholesterolemias in adult patients: recommendations from the National Lipid Association expert panel on familial hypercholesterolemia," Jun. 2011, pp. S38-S45, vol. 5, No. 35, Journal of Clinical Lipidology.

Maaskant, N. et al., "Removal of low density lipoprotein from blood plasma using cross-linked, sulfated polyvinylalcohol," 1986, pp. 159-166, vol. 62, Atherosclerosis.

Makino, H. et al., "Long-term effect of low-density lipoprotein apheresis in patients with homozygous familial hypercholesterolemia," 2003, pp. 397-401, vol. 7, No. 4, Therapeutic apheresis and dialysis.

Nazir, D. et al., "Monthly intra-individual variation in lipids over a 1-year period in 22 normal subjects," Jul. 1999, pp. 381-389, vol. 32, No. 5, Clinical Biochemistry.

Parhofer, K. et al., "Effects of weekly LDL-apheresis on metabolic parameters of apolipoprotein B in heterozygous familial hypercholesterolemia," 1996, pp. 2383-2393, vol. 37, Journal of Lipid Research.

Parker, T. et al., "Plasma high density lipoprotein is increased in man when low density lipoprotein (LDL) is lowered by LDL-pheresis," Feb. 1986, pp. 777-781, vol. 83, Proc. Natl. Acad. Sci. USA.

Saal, S. et al., "Removal of low-density lipoproteins in patients by extracorporeal immunoadsorption," Apr. 1986, pp. 583-589, vol. 80, No. 4, The American Journal of Medicine.

Schulzki, T. et al., "A prospective multicentre study on the safety of long-term intensive plasmapheresis in donors (SIPLA)," 2006, pp. 1-12, Vox Sanguinis.

Smart, N. et al., "Low-fat diets for acquired hypercholesterolaemia," 2011, pp. 1-21, vol. 2, The Cochrane Collaboration.

Stefanutti, C. et al., "Treatment of symptomatic HyperLp(a)lipoproteinemia with LDL-apheresis: a multicentre study," 2009, pp. 89-94, vol. 10, Atherosclerosis Supplements.

Stoffel, W. et al., "Application of specific extracorporeal removal of low density lipoprotein in familial hypercholesterolaemia," Nov. 7, 1981, pp. 1005-1007, vol. 318, No. 8254, The Lancet.

Szczepiorkowski, Z. et al., "Guidelines on the use of therapeutic apheresis in clinical practice-evidence-based approach from the apheresis applications committee of the American Society for Apheresis," 2007, pp. 106-175, vol. 22, Journal of Clinical Apheresis.

Takahashi, K. et al., "Long-term (14 years) effect of LDL apheresis on obstructive changes in aortocoronary saphenous-vein bypass grafts in a case of heterozygous familial hypercholesterolemia with the LDL receptor proline to leucine mutation," Oct. 2000, pp. 804-809, vol. 39, No. 10, Internal Medicine.

Tenenbaum, A. et al., "Atherogenic dyslipidemia in metabolic syndrome and type 2 diabetes: therapeutic options beyond statins," 2006, pp. 1-8, vol. 5, Cardiovascular Diabetology.

Thompsen, J. et al., "A systematic review of LDL aspheresis in the treatment of cardiovascular disease," 2006, pp. 31-38, vol. 189, Atherosclerosis.

Tran-Mi, B. et al., "The impact of different intensities of regular donor plasmapheresis on humoral and cellular immunity, red cell and iron metabolism, and cardiovascular risk markers," 2004, pp. 189-197, vol. 86, Vox Sanguinis.

(56) References Cited

OTHER PUBLICATIONS

Vella, A. et al., "Low-density lipoprotein apheresis for the treatment of refractory hyperlipidemia," Oct. 2001, pp. 1039-1046, vol. 76, Mayo Clinic Proceedings.

Yokoyama, S. et al., "Selective removal of low density lipoprotein by plasmapheresis in familial hypercholesterolemia," Nov./Dec. 1985, pp. 613-622, vol. 5, No. 6, Arteriosclerosis.

Ananchenko, VG., et al., "Plasmapheresis in the treatment of patients with hypertension," 1991, pp. 20-22, vol. 10, Sovereign Medical (abstract only).

Brown, C.W., et al., "Model for a one-step plasma treatment device: Feasibility of cholesterol removal," Nov./Dec. 1997, pp. 884-889, vol. 43, No. 6, ASAIO Journal.

Chang, W.D., et al., "An implementation of a WSN-based medical monitoring system: A pilot study of the blood pressure monitoring of hemodialysis patients," 2012, pp. 83-89, vol. 5, No. 3, Engineering in Agriculture, Environment and Food (abstract only).

Girard, A., et al., "Effects of plasmapheresis on short-term variability of blood pressure in healthy donors," Oct. 1992, pp. 299-302, vol. 2, No. 5, Clinical Autonomic Research (abstract only).

Mineshima, M., et al., "Continuous monitoring of blood volume in double filtration plasmapheresis," Sep./Oct. 1998, pp. M465-M469, vol. 44, No. 5, ASAIO Journal.

Tello, R., "Continuous noninvasive blood pressure monitoring during hemodialysis," 1984, p. 81, Association for Advancement of Medical Instrumentation, Proceedings—AAMI 19th Annual Meeting: Abstracts on the application of technology to health care (abstract only).

Final Office Action dated Oct. 22, 2015 for U.S. Appl. No. 13/418,123.

Rose Raymond (Selling your body?: Plasma donation: examining a growing trend, http://archive/voxmagazine.com/stories/2009/06/17/selling-your-body/, accessed Oct. 14, 2015, published Jun. 17, 2009).

Title 21-Food and Drugs, Part 640—Additional Standards for Human Blood and Blood Products—Subpart G—Source Plasma; 21 CFR 640.60-640.76 (http://www.gpo.gov/fdsys/granule/CFR-2010-title21-vol7/CFR-2010-title21-vol7-sec640-61, accessed Oct. 14, 2015).

Wayback Machine, https''//web.archive.org/web/*/http://www.inova.org/upload/docs/get%20involved/blood%20donor/ibds-factsheets.pdf, Accessed May 25, 2016.

Inova Blood Donor Services, http://www.inova.org/upload/docs/get%20involved/blood%20donor/ibds-factsheets.pdf, Saved Dec. 27, 2010.

Donating Blood and Cholesterol [Archive] Straight Dope Message Board (http://boards.straightdope.com/sdmb/archive/index.php/t221021.htm, Nov. 2, 2003, Accessed May 25, 2016).

Office Action dated Jun. 3, 2016 for U.S. Appl. No. 13/418,123.
Office Action dated Jun. 2, 2015 for U.S. Appl. No. 13/418,123.
Office Action (Advisory Action) dated Jan. 9, 2015 for U.S. Appl. No. 13/418,123.
Office Action dated Apr. 24, 2014 for U.S. Appl. No. 13/418,123.
Office Action dated Nov. 21, 2014 for U.S. Appl. No. 13/418,123.
Office Action (Advisory Action) dated Jan. 29, 2014 for U.S. Appl. No. 13/418,123.
Office Action dated Mar. 18, 2013 for U.S. Appl. No. 13/418,123.
Office Action dated Oct. 11, 2013 for U.S. Appl. No. 13/418,123.

* cited by examiner

USE OF PLASMAPHERESIS TO TREAT BLOOD PRESSURE DISORDERS

CROSS-REFERENCE TO RELATED APPLICATIONS

This application claims the benefit of priority of U.S. Provisional Application No. 62/006,999, filed Jun. 3, 2014, which application is incorporated by reference herein, in its entirety and for all purposes.

FIELD OF THE INVENTION

The present invention relates generally to methods for treating blood pressure disorders by administering multiple rounds of plasmapheresis.

BACKGROUND

Plasmapheresis is a common medical procedure whereby plasma is separated from whole blood. The whole blood is comprised principally of cellular components, i.e., red blood cells, white blood cells and platelets. Plasma is comprised largely of water, as well as proteins and various other non-cellular compounds, both organic and inorganic. Continuous plasmapheresis is a process of continuously removing whole blood from a subject, separating plasma from the blood, and returning the plasma-depleted blood to the subject in a continuous extracorporeal circuit. The blood can be returned to the body with replacement fluids, such as fresh plasma and/or an albumin solution. Plasmapheresis is currently used to obtain plasma for various reasons, including transfusion, preparation of fresh-frozen plasma, subsequent fractionation to obtain specific proteins such as serum albumin, cell culture media, and disease therapies involving either the replacement of plasma or removal of specific disease-contributing factors from the plasma.

When treating patients with therapeutic plasmapheresis, a catheter is typically placed in a large vein, such as in the arm, and a second catheter is placed in another vein, such as a vein in the foot or hand. Blood then passes out of the body via the catheter and through a separator. Plasma is separated from the whole blood. The blood without plasma, the desired fluids, and optional replacement fluids can be returned to the body via the second catheter. For plasma donations, automated plasmapheresis equipment is often used where a single venipuncture is required, as the blood is removed and returned through the same site.

There are several different types of therapeutic plasmapheresis including: (i) plasma exchange in which plasma that is separated and discarded is replaced with fresh plasma or an albumin solution, (ii) double filtration plasmapheresis in which plasma is passed through a separator with a small pore size so as to selectively remove large molecular weight proteins, or (iii) plasma adsorption in which plasma flows into a plasma adsorption column wherein certain substances can be adsorbed and removed. Plasmapheresis used for plasma donations typically uses centrifugation (e.g., Haemonetics blood processing systems) or centrifugation with a simple filter (e.g, Fenwal blood processing systems).

Numerous factors, including cardiac output, peripheral resistance, blood vessel elasticity, and blood volume, can affect a person's blood pressure (BP). The volume of plasma removed during plasmapheresis (e.g., 690-880 mL) is consistent with minimal physiological changes due to hypovolemia. However, the effect of plasmapheresis on blood pressure has rarely been reported. A treatment regime in which periodic plasmapheresis can be used to treat blood pressure disorders would be desirable.

SUMMARY OF THE INVENTION

An embodiment of the present invention provides a method of treating a blood pressure disorder comprising: identifying a patient having a blood pressure disorder, and administering a treatment regime comprising two or more rounds of plasmapheresis to the patient, wherein the treatment regime lowers blood pressure in the patient. According to particular embodiments, the patient has been diagnosed with Stage 1 hypertension or Stage 2 hypertension before administering the treatment regime, more preferably Stage 2 hypertension.

According to particular embodiments, each subsequent round of plasmapheresis is conducted 5-9 days after the previous round. Preferably, the method comprises administering a sufficient number of rounds of plasmapheresis to cause the patient's systolic blood pressure to be reduced by at least 10 mmHg and the patient's diastolic blood pressure to be reduced by at least 5 mmHg (as measured from immediately before the treatment regime has begun to immediately after the treatment regime has ended).

BRIEF DESCRIPTION OF THE FIGURES

The invention may be further understood by reference to the figures in which:

FIG. 1 illustrates the relationship between a change from baseline and baseline values for SBP (FIG. 1A) and DBP (FIG. 1B) in accordance with an embodiment of the invention;

FIG. 2 illustrates the effects of donations on changes from baseline SBP (FIG. 2A) and DBP (FIG. 2B) by blood pressure category in accordance with an embodiment of the invention;

FIG. 3 illustrates the goodness of fit between observed and predicted values for SBP (FIG. 3A), DBP (FIG. 3B), and heart rate using dynamic models in accordance with an embodiment of the invention.

DETAILED DESCRIPTION OF THE INVENTION

The applicants have discovered that systolic and diastolic blood pressure may be decreased following multiple plasmapheresis procedures in patients with high baseline blood pressure levels. In particular, the applicants have observed that significant decreases in systolic and diastolic blood pressure occur in patients with blood pressure disorders following multiple rounds of plasmapheresis. These decreases were observed, for example, in patients with Stage 1 and Stage 2 hypertension, with the most significant decreases occurring in patients with Stage 2 hypertension.

As used herein, the term "blood pressure disorder" denotes a disorder in which the systolic and/or diastolic blood pressure are abnormal. Non-limiting examples of blood pressure disorders include primary (or "essential") hypertension, secondary hypertension, malignant hypertension, isolated systolic hypertension, white coat hypertension, resistant hypertension, pulmonary hypertension, etc.

Hypertension, also known as high blood pressure (BP), sometimes called arterial hypertension, is a medical condition in which the blood pressure in the arteries is elevated. Blood pressure is determined by two measurements, systolic and diastolic, which depend on whether the heart muscle is contracting (systole) or relaxed between beats (diastole). Primary (or "essential") hypertension is the most common type of hypertension. Essential hypertension has no obvious or identifiable cause. Secondary hypertension is caused by an underlying condition, such as kidney problems, thyroid dysfunction, coarctation of the aorta, etc.

A patient may be determined to have normal blood pressure, prehypertension, Stage 1 hypertension, or Stage 2 hypertension in accordance with the criteria set forth in Table 1, which are adapted from The Seventh Report of the Joint National Committee on Prevention, Detection, Evaluation, and Treatment of High Blood Pressure, U.S. Department of Health and Human Services, NIH Publication No. 04-5230, August 2004.

TABLE 1

Blood Pressure Categories

| Category | Criteria | |
| --- | --- | --- |
| | SBP (mmHg) | DBP (mmHg) |
| Normal | <120 and <80 | |
| Prehypertension | 120-139 or 80-89 | |
| Stage 1 Hypertension | 140-159 or 90-99 | |
| Stage 2 Hypertension | ≥160 or ≥100 | |

An embodiment of the present invention provides a method of treating a blood pressure disorder comprising: identifying a patient having a blood pressure disorder, and administering a treatment regime comprising two or more rounds of plasmapheresis to said patient, wherein the treatment regime lowers blood pressure in said patient. A patient having a blood pressure disorder does not have normal blood pressure, and preferably does not have prehypertension. According to particular embodiments, the treatment regime lowers both systolic blood pressure and diastolic blood pressure in the patient. Before the treatment regime is administered, the patient has preferably been diagnosed with a blood pressure disorder, such as stage 1 hypertension, stage 2 hypertension, secondary hypertension, malignant hypertension, isolated systolic hypertension, white coat hypertension, resistant hypertension, or pulmonary hypertension. According to particular embodiments, the patient has been diagnosed with Stage 1 hypertension or Stage 2 hypertension before administering the treatment regime, more preferably Stage 2 hypertension. According to particular embodiments, the patient does not have a cholesterol disorder. However, it should be noted that a cholesterol disorder is not necessarily a contraindication to administering a treatment regime comprising two or more rounds of plasmapheresis to a patient. According to particular embodiments, the patient may have a cholesterol disorder and a blood pressure disorder, and the patient is administered a treatment regime comprising two or more rounds of plasmapheresis, wherein the treatment regime lowers blood pressure in the patient.

According to particular embodiments, the treatment regime comprises administering three or more rounds of plasmapheresis, four or more rounds of plasmapheresis, five or more rounds of plasmapheresis, six or more rounds of plasmapheresis, seven or more rounds of plasmapheresis, eight or more rounds of plasmapheresis, nine or more rounds of plasmapheresis, or ten or more rounds of plasmapheresis to the patient.

According to particular embodiments, each subsequent round of plasmapheresis is conducted 3-14 days after the previous round. According to alternative embodiments, each subsequent round of plasmapheresis is conducted 5-9 days after the previous round. Each subsequent round of plasmapheresis is more preferably conducted 5-7 days after the previous round, most preferably 5 days after the previous round. For example, a first round occurring on day 1 would be followed by a second round on day 6, a third round on day 11, etc. It should be understood that an individual undergoing multiple rounds of plasmapheresis in accordance with the invention may have one or more interruptions in treatment, i.e., more than 14 days may lapse after a round of plasmapheresis and before a subsequent round begins (e.g., 20 days, 30 days, 40 days, or more). In this case, the individual may return to the treatment by receiving a round of plasmapheresis (following the lapse of more than 14 days) and by receiving each subsequent round of plasmapheresis 3-14 days after the previous round. Thus, the invention contemplates that individuals who have had an interruption in treatment may return to the 3-14 day cycle and have the benefits of the treatment restored.

According to particular embodiments, the method comprises administering a sufficient number of rounds of plasmapheresis to cause the patient's systolic blood pressure to be reduced by at least 10 mmHg and the patient's diastolic blood pressure to be reduced by at least 5 mmHg (as measured from immediately before the treatment regime has begun to immediately after the treatment regime has ended). According to additional embodiments, the method comprises administering a sufficient number of rounds of plasmapheresis to cause the patient's systolic blood pressure to be reduced by at least 12 mmHg and the patient's diastolic blood pressure to be reduced by at least 6 mmHg. According to additional embodiments, the method comprises administering a sufficient number of rounds of plasmapheresis to cause the patient's systolic blood pressure to be reduced by at least 14 mmHg and the patient's diastolic blood pressure to be reduced by at least 7 mmHg. According to additional embodiments, the method comprises administering a sufficient number of rounds of plasmapheresis to cause the patient's systolic blood pressure to be reduced by at least 16 mmHg and the patient's diastolic blood pressure to be reduced by at least 8 mmHg. According to additional embodiments, the method comprises administering a sufficient number of rounds of plasmapheresis to cause the patient's systolic blood pressure to be reduced by at least 18 mmHg and the patient's diastolic blood pressure to be reduced by at least 9 mmHg.

According to particular embodiments, each round of plasmapheresis involves automated plasmapheresis using a single venipuncture. Any extracorporeal plasmapheresis device known in the art may be used in accordance with the present invention. For example, the device may include an entrance port for receiving the whole blood from a patient, means for separating plasma from the cellular components of the blood, and a means for returning the cellular components of the blood through the entrance port from where the blood cellular components exited the device, and an exit port from where the plasma exits the device. Preferably, the means for separating plasma from the cellular components of the blood are centrifugation means (i.e., a centrifuge). More preferably, the means for separating plasma from the cellular components of the blood are filtration means (i.e., a filter such as that used in double filtration plasmapheresis).

According to a particular embodiment, a method of treating a blood pressure disorder comprises: identifying a patient having systolic blood pressure of at least 160 mmHG and/or diastolic blood pressure of at least 100 mmHg (or identifying a patient having systolic blood pressure of at least 140 mmHg and/or diastolic blood pressure of at least 90 mmHg); and administering a treatment regime comprising five or more rounds of plasmapheresis to said patient, with each subsequent round of plasmapheresis conducted 3-14 days after the previous round (or 5-7 days after the previous round), wherein the treatment regime reduces the patient's systolic blood pressure by at least 10 mmHg and diastolic blood pressure by at least 5 mmHg, as measured from immediately before the treatment regime has begun to immediately after the treatment regime has ended.

EXAMPLE

Embodiments of the present invention may be further understood by reference to the Example provided below.

A 16-week study with healthy donors was conducted. From this study, the vital signs obtained prior to each donation were analyzed using statistical and dynamic analytical predictive models to determine if there were any prolonged effects of plasma donation on blood pressure.

Study Design

Participants in the prospective, longitudinal cohort trial were 18-69 years old and were new donors or previous donors from 9 US donation centers who had not donated for at least 6 months. Donors met all industry standards for plasma donation, including all standard BP requirements for donor participation [3]. A diagnosis of hypertension was acceptable for donation as was the use of anti-hypertensive medications, except beta-blockers. Qualifying donors who elected to participate in the study signed a separate consent for study participation. Participants were asked to donate at least once weekly for 16 weeks, and 2 donations in any 7 day period were permitted per FDA guidelines.

Vital Signs Measurements

Blood pressure was measured prior to donation using electronic vital signs measurement systems from Welch Allyn (Skaneateles Falls, N.Y.) or IVAC (San Diego, Calif.). Machines were calibrated daily and are routinely inspected at 6-month intervals to insure accurate data collection.

Based on the time required for routine donor center procedures, donors were expected to have been at the site at least 15 minutes before BP measurements were obtained.

Statistical Analysis

Participants were assigned to 1 of 4 baseline BP groups (normal, prehypertensive, Stage 1 hypertension, Stage 2 hypertension) according to the classification of the Joint National Committee on Prevention, Detection, Evaluation and Treatment of High Blood Pressure of the NHLBI [15].

An exploratory graphical analysis was conducted by examining the relationships and calculating correlation coefficients between candidate explanatory variables baseline value, days since first observation, time since last donation, donation count, and an estimate of the rate of donations (cumulative number of donations divided by elapsed time since start) and the endpoints of interest: change in systolic blood pressure (SBP) and diastolic blood pressure (DBP). These results provide a univariate view of possibly interdependent effects, and statistical and dynamic models were later developed to further explore the results.

Statistical models were used to quantify the effect of donation after adjusting for the potential effect of baseline SBP and DBP values. The donor's baseline BP category was treated as a categorical variable and was included in the statistical models by default to remedy potential regression to the mean effects. The tested statistical models consisted of generalized additive models that tested linear and non-linear effects of donation counts in addition to testing the potential interactions between the various explanatory variables. The final statistical models for SBP and DBP had the following general equation:

Δ=Intercept+Baseline Cat+Donation Count+Interaction (Baseline Cat/Donation Count) where baseline category was a categorical variable and donation count was modeled using a flexible restrictive cubic spline. The restrictive cubic spline avoids assuming a linear relationship since it can take various forms according to the trends dictated by the data.

Finally, semi-mechanistic longitudinal mixed effects models (Dynamic indirect-response models) were tested. These flexible models assume that there is an endogenous homeostatic process involving a formation process as well as degradation processes which help in maintaining the stability of the modeled endpoints (SBP, DBP). The effects of explanatory variables (Donation and the patterns of donations across time) were then constructed using a compartment which allowed them to accumulate or wear down according the donation frequency and time between donations.

The accumulated donation effect was tested as a covariate on the parameter representing the formation or the degradation of the modeled physiological endpoint [16, 17]. The dynamic model also used the baseline values as a covariate in the model to adjust for a potential regression to the mean effect. The potential delay between the donation event and the BP change was also tested by including a delay compartment.

The semi-mechanistic longitudinal mixed effects models (dynamic indirect-response models) employed to predict changes in SBP and DBP following plasma donation in a group of plasma donors is summarized using the following equations.

Differential Equation of Donation Effect:

$$\frac{dDonation_{acc}}{dt} = \text{Donation Event(Time)} - \text{Rate of Donation Effect} * \text{Time}$$

Differential Equation of Donation Effect Delay:

$$\frac{dDonation_{accdelay}}{dt} = k_s0 * (Donation_{acc} - Donation_{accdelay})$$

Differential Equation of the Homeostatic Process (SBP or DBP):

$$\frac{dEndo_{homeostatic}}{dt} = k_{in} - k_{out} \times Endo_{homeostatic}$$

where baseline value of $$Endo_{homeostatic} = \frac{k_{in}}{k_{out}}$$

Donation Effect on the Homeostatic Process when Delay is Incorporated:

$$(1-I_1\max * \llbracket Donation \rrbracket_{accdelay}/(\llbracket IC \rrbracket_{50} + \llbracket Donation \rrbracket_{accdelay})$$

where
$I_{max}$ is the maximum possible donation effect that can be modeled as a function of the baseline value.
$IC_{50}$ is the value of the Donation$_{accdelay}$ that results in a half maximum effect.
Donation$_{accdelay}$ takes into account all the donation history of the donor up to the time where the modeled variable value is measured.

When donation is affecting the generation of the homeostatic process the differential equation of the homeostatic process (SBP or DBP) becomes:

$$\frac{dEndo_{homeostatic}}{dt} = k_{in} * \left(1 - I_{max} * \frac{Donation_{accdelay}}{(IC_{50} + Donation_{accdelay})}\right) - k_{out} * Endo_{homeostatic}$$

where Endo is the endogenous process, $k_{in}$ is the zero order rate of input and $k_{out}$ is the first order rate of output.

The graphical analysis of relationship and correlations as well as the general linear models were performed using R, version 2.15.3 (2013; R Foundation for Statistical Computing, Vienna, Austria). The package rms was used to fit the models and conduct the statistical tests. Dynamic models were fitted using the Phoenix™ NLME version 1.3 with the Lindstrom-Bates first-order conditional estimation method (FOCE-L-B).

Results

Overall, 666 donors were studied (407 males and 259 females). Two donors with data for only 1 donation were included in the analysis as part of the baseline (intercept fit) calculation. Baseline BP was normal in 29.8% of donors while 44.9% presented with prehypertension (Table 2). Baseline levels consistent with Stage 1 and Stage 2 hypertension were observed in 22.1% and 3.5% of donors, respectively.

TABLE 2

Baseline Blood Pressure Categories

| Category* | Criteria | | n (%) |
|---|---|---|---|
| | SBP (mmHg) | DBP (mmHg) | |
| Normal | <120 and <80 | | 197 (29.8) |
| Prehypertension | 120-139 or 80-89 | | 299 (44.9) |
| Stage 1 Hypertension | 140-159 or 90-99 | | 147 (22.1) |
| Stage 2 Hypertension | ≥160 or ≥100 | | 23 (3.5) |

Figure 1A:
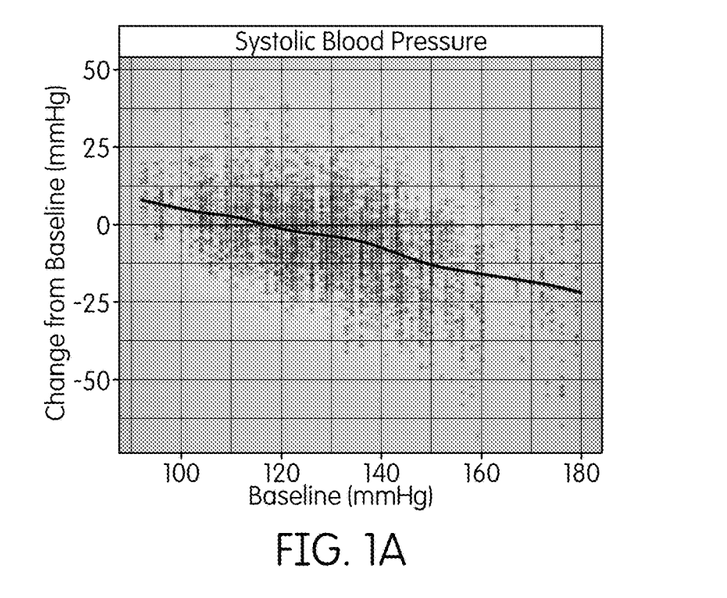
Figure 1B:
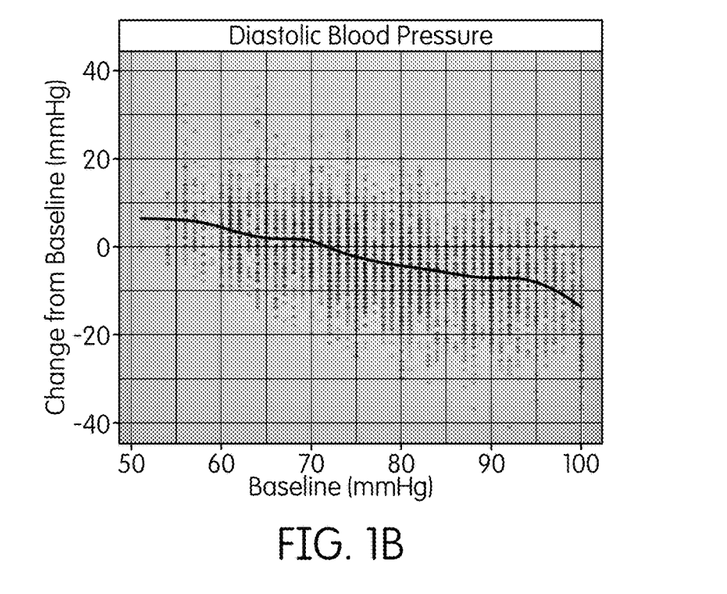

*Seventh Report of the Joint National Committee on Prevention, Detection, Evaluation, and Treatment of High Blood Pressure Exploratory Analysis A plot of change in SBP vs baseline SBP suggested that donors with higher baseline SBP showed greater SBP decreases (FIG. 1a). A moderate negative correlation (correlation coefficient −0.44) was calculated, suggesting that donors with higher baseline SBP had a greater change from baseline following donation (Table 3). Similarly, change in DBP had a moderate negative correlation with baseline DBP (FIG. 1b, Table 3). The relationships between change from baseline SBP and DBP and donation counts were weakly negative, with correlation coefficients of −0.15 and −0.098 for SBP and DBP, respectively.

TABLE 3

Correlation between Change from Baseline and Possible Explanatory Variables for SBP and DBP

| | Correlation Coefficient* | |
|---|---|---|
| | SBP (mmHg) | DBP (mmHg) |
| Baseline Value (mmHg) | −0.44 | −0.47 |
| Days Since First Donation (days) | −0.10 | −0.05 |
| Time Since Last Donation (days) | 0.048 | 0.04 |
| Cumulative donation counts | −0.15 | −0.098 |
| Rate of Donation** | −0.01 | −0.059 |

Figure 2A:
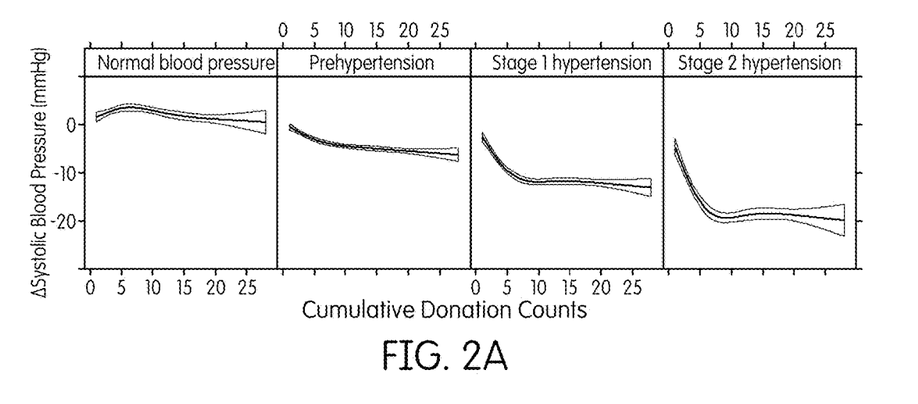

*Pearson correlation coefficient
**Cumulative number of donation divided by elapsed time since start in days Statistical Model For SBP, baseline BP category and donation count were both statistically significant with an interaction term (p<0.0001 for all the model terms: donation counts, BP category and their interaction). The model-predicted effect of SBP is presented by BP group in FIG. 2a. Almost no effect was predicted for donors with normal BP, with mean change ranging from +0.37 to +3.21 mmHg; a similar magnitude of change (mean −0.30 to −5.75 mmHg) was predicted in the group with baseline measurements in the prehypertensive range. More pronounced changes were predicted in donors with baseline measurements in the Stage 1 and Stage 2 ranges, with changes increasing as the number of donations increased. Donors with baseline measurements in the Stage 2 hypertension range showed marked predicted decreases in SBP during the first 2-5 donations which were maintained for the duration of the study (mean change −4.00 to −21.65 mmHg), with similar but more modest changes (−3.01 to −14.87 mmHg) predicted for those with baseline measurements in the Stage 1 hypertension range.

Figure 2B:
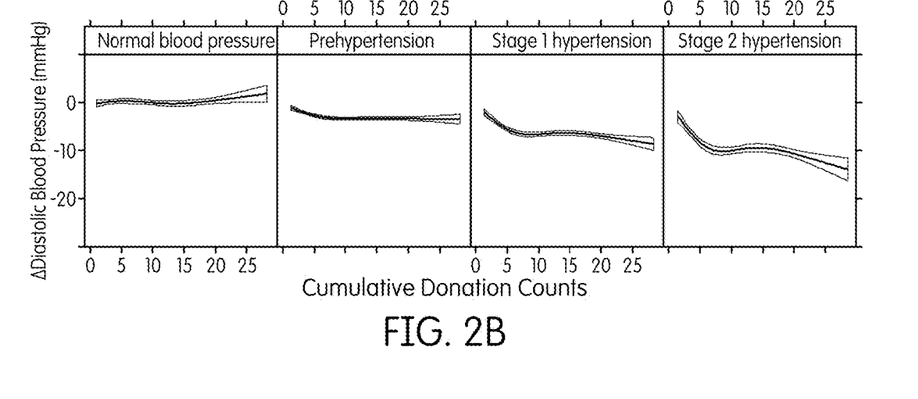

Similar results were predicted for DBP (FIG. 2b). Almost no change was predicted in donors with normal baseline BP (mean change −0.54 to +0.35 mmHg). The greatest predicted change in DBP (mean change 2.13 to −16.73 mmHg) was in donors with baseline Stage 2 pressures. As with SBP, BP category and donation count were both statistically significant (p<0.0001) with a significant interaction (p<0.0001) observed between BP category and donation count.

Dynamic Model

Figure 3A:
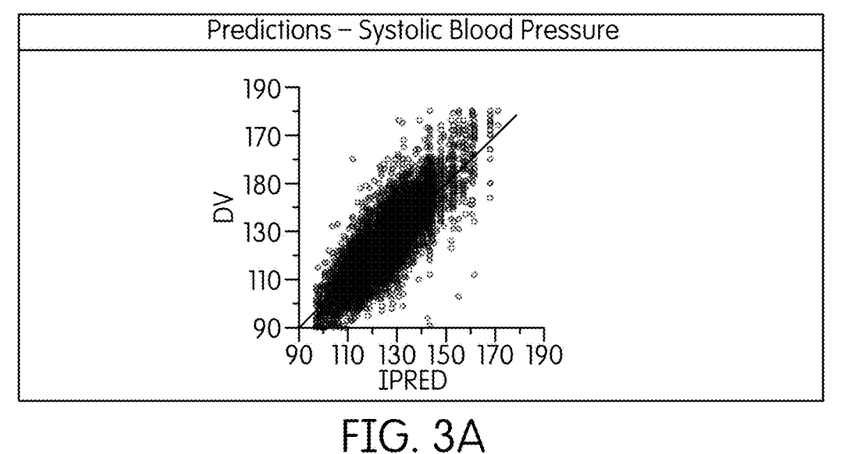
Figure 3B:
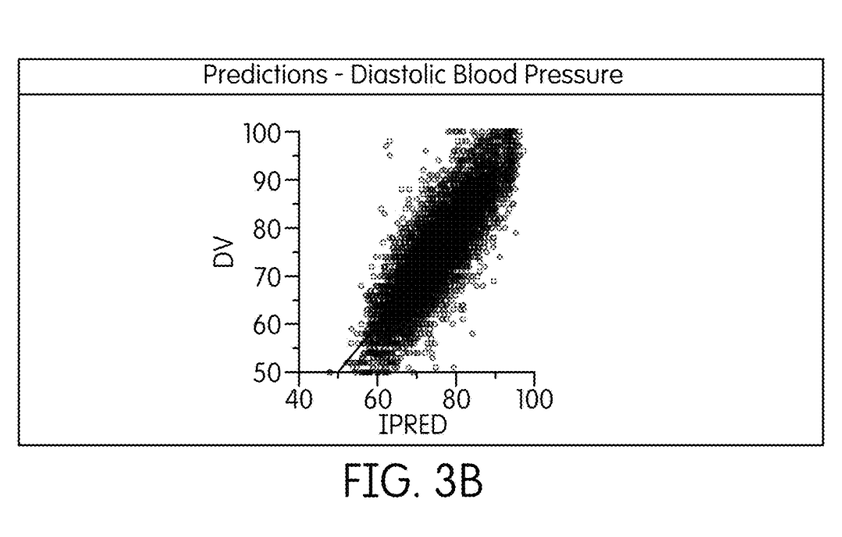

Since the statistical model did not consider the possible effect of time between donations in a mechanistic way, a dynamic model was constructed to test these effects. As shown by comparison of observed and predicted values, the dynamic model resulted in an acceptable quality of fit for SBP and DBP (FIG. 3). The effect of donations on mean predicted individual changes in SBP and DBP is summarized in Table 4. Minimal decreases in SBP and DBP were predicted for donors with baseline normal BP while marked decreases in SBP (−19.5 mmHg) and DBP (−9.05 mmHg) were predicted for donors with baseline BP in the Stage 2 hypertension range.

TABLE 4

Effect of Plasma Donations on Mean Predicted Change in SBP and DBP by Baseline BP Category, Dynamic Model

| Baseline BP Category | Mean Predicted Change | |
|---|---|---|
| | SBP (mmHg) | DBP (mmHg) |
| Normal | −3.34 | −2.62 |
| Prehypertension | −6.46 | −4.36 |
| Stage 1 Hypertension | −11.7 | −6.51 |
| Stage 2 Hypertension | −19.5 | −9.05 |

Figure 4:
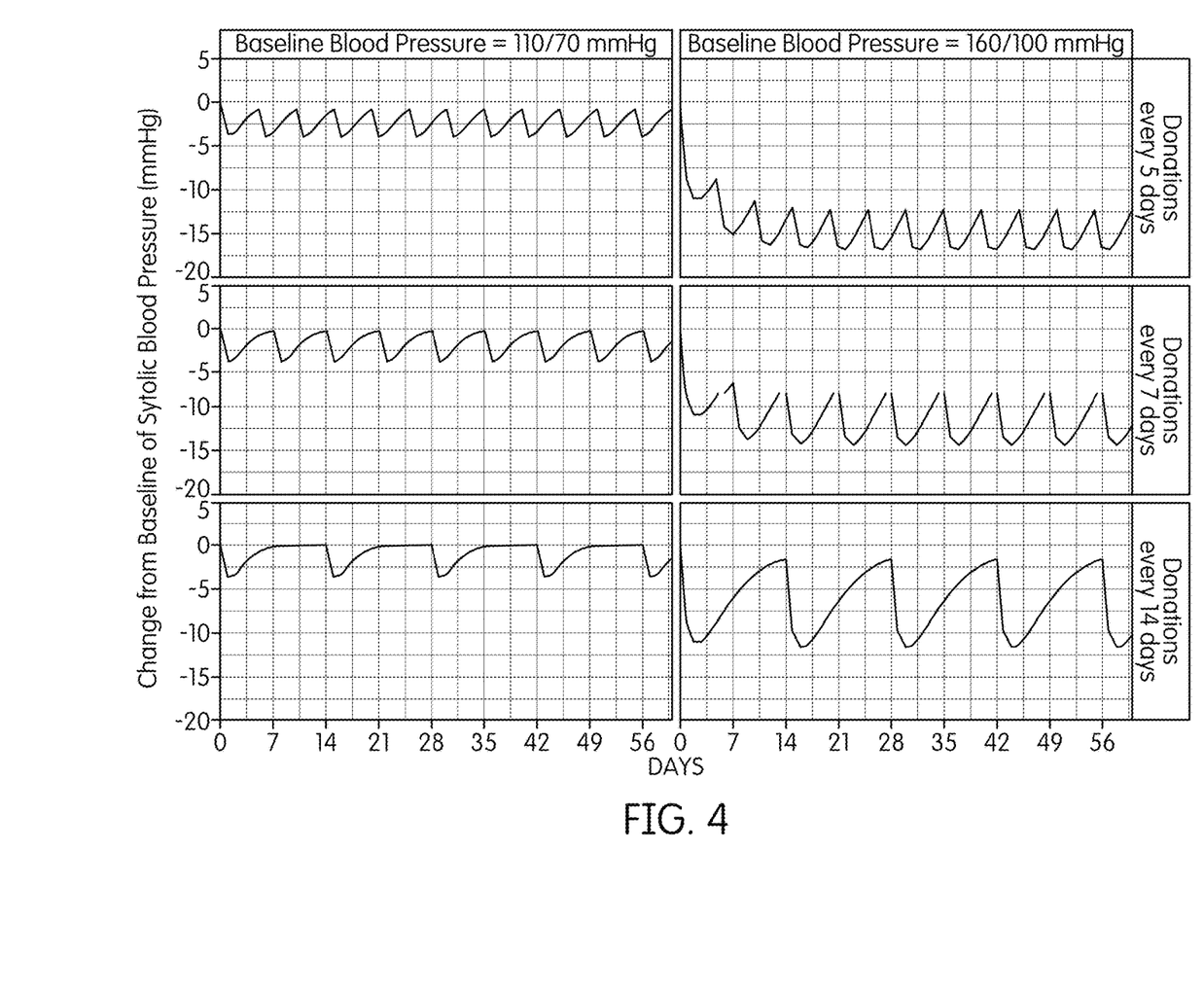
FIG. 4 illustrates the effect of donation interval on predicted changes in SBP in baseline normotensive and Stage 2 hypertensive donors in accordance with an embodiment of the invention.

The predicted effect of donation interval in donors with normotensive and Stage 2 hypertensive baseline readings is presented in FIG. 4. Using a 5-day donation interval, baseline SBP in Stage 2 hypertensive donors decreased markedly following the first 2 donations with SBP 16-17 mmHg below baseline modeled for all subsequent donations and a recovery of approximately 4-5 mmHg predicted between donations. With a 14 day donation interval, the dynamic model predicted a maximum SBP drop of 11-12 mmHg and a full recovery to baseline levels. In contrast, SBP modeling of donors with normotensive baseline measurements showed a maximum drop of 3-4 mmHg following plasmapheresis with a recovery to baseline levels within 5-6 days post donation. Modeling of DBP predicted a drop of approximately 5 mmHg following 2 donations and for all subsequent donations which recovered to within 1-2 mmHg of baseline levels in the 5 day interval. With 7 and 14 day donation intervals, similar drops in DBP with a full recovery to baseline levels within 7 days were predicted.

The results of the study suggest that BP levels can be affected following plasmapheresis in some donor groups. Although almost no change was observed in donors with normal baseline SBP or DBP, a decrease in BP was observed after the first 2-5 donations in donors with baseline BP in the Stage 2 hypertension range. Similarly, smaller decreases in SBP and DBP were observed in those donors with baseline Stage 1 hypertension. The significant interaction observed between baseline BP category and donation count suggests that the higher the baseline BP category, the greater the donation effect.

The BP changes predicted by the statistical and dynamic models were similar. Although the statistical model did not examine the effect of time between donations, the dynamic model predicted a return to baseline levels between donations for a donation interval of 14 days. However, with 5 or 7 day donation interval, SBP and, to a lesser extent, DBP was markedly reduced with only partial recovery predicted between donations.

The BP changes appear to be highly dependent on the donor's baseline BP category and, while the possibility of some regression to the mean effect cannot be completely excluded, the use of baseline BP category in the model by default was intended to minimize this possibility.

This study suggests that plasma donation is well tolerated and lowers both SBP and DBP in donors with baseline blood pressure within the ranges for Stage 1 and Stage 2 hypertension. These decreases in BP appeared to persist with a frequent donation schedule (e.g., about 5 days).

Although the present invention has been described in connection with specific embodiments, it should be understood that the invention as claimed should not be unduly limited to such specific embodiments. Indeed, various modifications and variations of the described compositions and methods of the invention will be apparent to those of ordinary skill in the art and are intended to be within the scope of the appended claims.

What is claimed is:

1. A method of treating primary hypertension, comprising:
    identifying a patient having primary hypertension, wherein the patient has a blood pressure and the patient lacks a cholesterol disorder;
    identifying that the patient has primary hypertension;
    administering a treatment regimen to the patient comprising two or more rounds of plasmapheresis, wherein the two or more rounds comprise a first round of plasmapheresis and one or more subsequent rounds of plasmapheresis, and each subsequent round of plasmapheresis is conducted 5-7 days after the immediately preceding round of the two or more rounds;
    administering the first round of plasmapheresis to the patient;
    administering a second round of plasmapheresis to the patient 5-7 days after the first round, wherein the second round is a subsequent round of plasmapheresis that immediately precedes the first round; and
    lowering the blood pressure of the patient to thereby treat primary hypertension.

2. The method of claim 1, further comprising identifying that the patient has Stage 1 hypertension or Stage 2 hypertension.

3. The method of claim 1, wherein the patient has a systolic blood pressure and a diastolic blood pressure, further comprising lowering both the systolic blood pressure and the diastolic blood pressure of the patient.

4. The method of claim 1, further comprising administering a third round of plasmapheresis to the patient after administering the second round of plasmapheresis, wherein the treatment regimen comprises administering three or more rounds of plasmapheresis to the patient and the third round is a subsequent round.

5. The method of claim 4, further comprising:
    administering a fourth round of plasmapheresis to the patient after administering the third round of plasmapheresis; and
    administering a fifth round of plasmapheresis to the patient after administering the fourth round,
    wherein the treatment regimen comprises administering five or more rounds of plasmapheresis to the patient, and the fourth round and the fifth round are subsequent rounds.

6. The method of claim 1, wherein each round of plasmapheresis comprises automated plasmapheresis using a single venipuncture.

7. The method of claim 3, further comprising lowering the systolic blood pressure by at least 10 mmHg and lowering the diastolic blood pressure by at least 5 mmHg.

8. The method of claim 3, further comprising lowering the systolic blood pressure by at least 16 mmHg and lowering the diastolic blood pressure by at least 8 mmHg.

9. The method of claim 1, further comprising:
    identifying that the patient has either a systolic blood pressure of at least 140 mmHg or a diastolic blood pressure of at least 90 mmHg; and
    identifying that the patient has a systolic blood pressure less than 160 mmHg and a diastolic blood pressure less than 100 mmHg.

10. The method of claim 1, wherein each round of plasmapheresis comprises automated plasmapheresis using a single venipuncture, wherein the blood of the patient is removed and returned through the same site.

11. A method of treating primary hypertension in a human patient, comprising:
   identifying a patient having primary hypertension;
   identifying that the patient has stage 1 hypertension;
   administering to the patient two or more rounds of plasmapheresis; and
   lowering the blood pressure of the patient to thereby treat primary hypertension,
   wherein:
   each round of plasmapheresis is automated plasmapheresis using a single venipuncture, wherein the blood of the patient is removed and returned through the same site;
   stage 1 hypertension is defined as (1) either a systolic blood pressure of at least 140 mmHg or a diastolic blood pressure of at least 90 mmHg, and (2) a systolic blood pressure less than 160 mmHg and a diastolic blood pressure less than 100 mmHg; and
   the patient has primary hypertension.

12. The method of claim 11, wherein the patient has a systolic blood pressure, further comprising lowering the systolic blood pressure of the patient to less than 140 mmHg.

13. The method of claim 11, wherein each round of plasmapheresis is administered 5 to 9 days after the prior round.

14. The method of claim 11, wherein the patient lacks a cholesterol disorder.

15. The method of claim 11, wherein the patient lacks a disease or condition that impairs kidney function.

16. The method of claim 11, further comprising lowering the systolic blood pressure of the patient to less than 140 mmHg, wherein:
   each round of plasmapheresis is administered 5 to 9 days after the prior round; and
   the patient lacks a disease or condition that impairs kidney function.

17. A method of treating primary hypertension in a human patient, comprising:
   identifying a patient having a systolic blood pressure of at least 140 mmHg or a diastolic blood pressure of at least 90 mmHg;
   identifying that the patient has primary hypertension;
   administering to the patient two or more rounds of plasmapheresis; and
   lowering the blood pressure of the patient to thereby treat primary hypertension,
   wherein:
   each round of plasmapheresis is automated plasmapheresis using a single venipuncture, wherein the blood of the patient is removed and returned through the same site;
   the patient lacks a cholesterol disorder; and
   the patient lacks a disease or condition that impairs kidney function.

18. The method of claim 17, further comprising lowering the systolic blood pressure of the patient to less than 140 mmHg.

19. The method of claim 17, wherein each round of plasmapheresis is administered 5 to 9 days after the prior round.

20. The method of claim 17, further comprising identifying that the patient has both (1) either a systolic blood pressure of at least 140 mmHg or a diastolic blood pressure of at least 90 mmHg, and (2) a systolic blood pressure less than 160 mmHg and a diastolic blood pressure less than 100 mmHg.

* * * * *